United States Patent
Ueda et al.

(10) Patent No.: US 11,510,286 B2
(45) Date of Patent: Nov. 22, 2022

(54) HEATER TEMPERATURE CONTROL CIRCUIT AND SENSOR DEVICE USING THE SAME

(71) Applicant: KOA CORPORATION, Nagano (JP)

(72) Inventors: Toshitsugu Ueda, Fukuoka (JP); Hiroshi Oigawa, Nagano (JP); Mitsuo Ohashi, Nagano (JP); Mizuho Shimojima, Nagano (JP); Takaaki Yano, Nagano (JP)

(73) Assignee: KOA CORPORATION, Nagano (JP)

( * ) Notice: Subject to any disclaimer, the term of this patent is extended or adjusted under 35 U.S.C. 154(b) by 275 days.

(21) Appl. No.: 16/767,775

(22) PCT Filed: Nov. 28, 2018

(86) PCT No.: PCT/JP2018/043863
§ 371 (c)(1),
(2) Date: May 28, 2020

(87) PCT Pub. No.: WO2019/107446
PCT Pub. Date: Jun. 6, 2019

(65) Prior Publication Data
US 2020/0296800 A1    Sep. 17, 2020

(30) Foreign Application Priority Data
Nov. 30, 2017   (JP) .............................. JP2017-230501

(51) Int. Cl.
*F02D 41/14*   (2006.01)
*H05B 1/02*   (2006.01)
(Continued)

(52) U.S. Cl.
CPC ....... *H05B 1/0297* (2013.01); *F02D 41/1494* (2013.01); *G01N 33/0016* (2013.01); *G05D 23/19* (2013.01); *H03M 1/66* (2013.01)

(58) Field of Classification Search
CPC .. H05B 1/0297; G01N 33/0016; G05D 23/19; H03M 1/66; F02D 41/1494
See application file for complete search history.

(56) References Cited

U.S. PATENT DOCUMENTS 3,647,969 A * 3/1972 Korn ...................... H04R 3/002
                                                                 330/106
4,086,466 A * 4/1978 Scharlack .......... G05D 23/2401
                                                                 219/505
(Continued)

FOREIGN PATENT DOCUMENTS

EP           0293255 A2 *  11/1988
JP         2007-245489 A     9/2007
(Continued)

OTHER PUBLICATIONS

International Search Report, dated Mar. 5, 2019 by the Japan Patent Office, in International Application No. PCT/JP2018/043863.

*Primary Examiner* — Dinh T Le
(74) *Attorney, Agent, or Firm* — Greenblum & Bernstein, P L C.

(57) ABSTRACT

The present invention provides a heater temperature control circuit including a heater and a control circuit that controls a temperature of the heater, wherein the control circuit includes a bridge circuit in which a first circuit and a second circuit are connected in parallel, and an operational amplifier connected to the bridge circuit, wherein in the first circuit, the heater and a resistor are connected in series, and a midpoint of the first circuit is connected to one input portion of the operational amplifier, and an output value $V_{out}$ from the second circuit is input to the other input portion of the operational amplifier, the output value $V_{out}$ being obtained by multiplying a division ratio of a target resistance value $R_h$
(Continued)

of the heater and a resistance value $R_1$ of the resistor with a reference voltage $V_{ref}$ of the bridge circuit.

6 Claims, 4 Drawing Sheets

(51) Int. Cl.
    *G01N 33/00*     (2006.01)
    *G05D 23/19*     (2006.01)
    *H03M 1/66*     (2006.01)

(56) References Cited

U.S. PATENT DOCUMENTS

| | | |
|---|---|---|
| 6,994,777 B2 * | 2/2006 | Gonzalez-Martin .......... G01N 27/126 204/406 |
| 2007/0216714 A1 | 9/2007 | Sato |
| 2015/0185061 A1 | 7/2015 | Otsuka et al. |

FOREIGN PATENT DOCUMENTS

| | | |
|---|---|---|
| JP | 2011-185742 A | 9/2011 |
| JP | 2012-251975 A | 12/2012 |
| JP | 2013-088918 A | 5/2013 |
| JP | 2015-125033 A | 7/2015 |
| JP | 2017-054340 A | 3/2017 |

* cited by examiner

HEATER TEMPERATURE CONTROL CIRCUIT AND SENSOR DEVICE USING THE SAME

TECHNICAL FIELD

The present invention relates to a heater temperature control circuit and a sensor device using the same.

BACKGROUND ART

Patent Literature 1 and Patent Literature 2 each disclose the invention relating to a temperature control device of a micro heater.

As illustrated in FIG. 1 of Patent Literature 1 and FIG. 2 of Patent Literature 2, there is widely known a temperature control device of a feedback control scheme including a Wheatstone bridge and a driving operational amplifier connected to the Wheatstone bridge.

In Patent Literature 1 and Patent Literature 2, a micro heater is used for an oxygen concentration device and an alcohol concentration detection device.

Incidentally, to improve the detection accuracy of the gas concentration, it is necessary to provide a control circuit with high accuracy which can maintain a constant temperature of the heater.

CITATION LIST

Patent Literature

Patent Literature 1: Japanese Patent Laid-Open. No. 2011-185742
Patent Literature 2: Japanese Patent Laid-Open No. 2012-251975

SUMMARY OF INVENTION

Technical Problem

However, in a conventional temperature control device, a temperature error depending on the accuracy of a resistor occurs, the resistor being used for a heater temperature control circuit. Therefore, the heater temperature cannot be maintained at a constant value with high accuracy. The conventional problem will be described with reference to the drawings. FIG. 6 is a minimum unit of the conventional heater temperature control circuit.

As illustrated in FIG. 6, the Wheatstone bridge is formed to include a heater 100, and resistors 101, 102, and 103. As illustrated in FIG. 6, the resistor 101 and the heater 100 are connected in series, and a midpoint thereof (output portion) 104 is connected to an inverting input terminal ($V_{in}$− terminal) 105a of an operational amplifier 105. In addition, the resistor 102 and the resistor 103 are connected in series, and a midpoint thereof (output portion) 106 is connected to a non-inverting input terminal ($V_{in}$+ terminal) 105b of the operational amplifier 105.

The equilibrium condition of the bridge circuit illustrated in FIG. 6 is expressed by the following expression (1).

$$R_h = \frac{R_1}{R_2} R_3 \quad (1)$$

where $R_h$ is a resistance value at a heater temperature (target temperature) in stabilization.

In the heater temperature control circuit illustrated in FIG. 6, by determining the resistance values $R_1$, $R_2$, and $R_3$ of the respective resistors 101, 102, and 103, a negative feedback is automatically applied, whereby the circuit operates so that the heater 100 is stabilised at the target temperature.

Incidentally, each of the resistance values $R_1$, $R_2$, and $R_3$ of the respective resistors 101, 102, and 103 has an inherent resistance value tolerance and temperature coefficient of resistance (TCR).

Thus, the expression (1) is expressed by the following expression (2) from the viewpoint of the resistance value tolerance and the temperature coefficient of resistance (TCR).

$$R_h = \frac{(1+E_1+E_{T1})R_1}{(1+E_2+E_{T2})R_2} \times (1+E_3+E_{T3})R_3 \quad (2)$$

$E_1$, $E_2$, $E_3$: Resistance value tolerance of each resistor
$E_{T1}$, $E_{T2}$, $E_{T3}$: Error caused by temperature coefficient of resistance (TCR) of each resistor
$E_T = TCR \times \Delta T_r$
$\Delta T_r$: External air temperature change Therefore, it is inevitable that an error occurs in $R_h$ determined according to the bridge equilibrium condition.

This error consequently appears as a deviation of a stable point of the heater temperature with respect to the target temperature.

Here, the target resistance value Rh is defined by the following expression (3).

$R_h = R_0(1+TCR\,(T_h-T_0))$ (3)
$T_h$: Heater temperature in stabilization
$T_0$: Reference temperature
$R_0$: Resistance value of heater at reference temperature The heater temperature in stabilization (target temperature) can be calculated as shown in the following expression (4), by using the expression (3).

$$T_h = \frac{1}{TCR} \cdot \frac{R_h - R_0}{R_0} + T_0 \quad (4)$$

However, as shown in the above expression (2), in the heater temperature control circuit in FIG. 6, an error occurs in the target resistance value $R_h$. As the worst case, when the error occurs to increase the resistance values $R_1$ and $R_3$ and the error occurs to reduce the resistance value $R_2$, the error in the target resistance value $R_h$ becomes extremely large.

Accordingly, the temperature accuracy of the heater 100 cannot be improved, which is likely to cause low sensor sensitivity and high variability of the sensor device using the heater 100.

Therefore, the present invention has been made in view of the above problem, and an object of the present invention is to provide a heater temperature control circuit that can control a heater temperature with higher accuracy than the conventional one and a sensor device using the same.

Solution to Problem

The present invention provides a heater temperature control circuit that controls a temperature of a heater, the heater temperature control circuit including a bridge circuit in which a first circuit and a second circuit are connected in parallel, and an operational amplifier connected to the bridge circuit, wherein in the first circuit, the heater and a resistor are connected in series, and a midpoint of the first circuit is connected to one input portion of the operational amplifier, and an output value $V_{out}$ from the second circuit is input to the other input portion of the operational amplifier, the output value $V_{out}$ being obtained by multiplying a division ratio of a target resistance value of the heater and a resistance value $R_1$ of the resistor with a reference voltage $V_{ref}$ of the bridge circuit.

The present invention provides a heater temperature control circuit that controls a temperature of a heater, the heater temperature control circuit including a bridge circuit in which a first circuit and a second circuit are connected in parallel, and an operational amplifier connected to the bridge circuit, wherein the first circuit includes the heater, and a midpoint of the first circuit is connected to one input portion of the operational amplifier, and the second circuit includes a D/A converter or a multiplexer, and an output portion of the D/A converter or the multiplexer is connected to the other input portion of the operational amplifier.

A sensor device of the present invention includes a sensor element, a heater that applies heat to the sensor element, and a heater temperature control circuit that controls a temperature of the heater, wherein the heater temperature control circuit includes a bridge circuit in which a first circuit and a second circuit are connected in parallel, and an operational amplifier connected to the bridge circuit, in the first circuit, the heater and a resistor are connected in series, and a midpoint of the first circuit is connected to one input portion of the operational amplifier, and an output value $V_{out}$ from the second circuit is input to the other input portion of the operational amplifier, the output value $V_{out}$ being obtained by multiplying a division ratio of a target resistance value $R_h$ of the heater and a resistance value $R_1$ of the resistor with a reference voltage $V_{ref}$ of the bridge circuit.

A sensor device of the present invention includes a sensor element, a heater that applies heat to the sensor element, and a heater temperature control circuit that controls a temperature of the heater, wherein the heater temperature control circuit includes a bridge circuit in which a first circuit and a second circuit are connected in parallel, and an operational amplifier connected to the bridge circuit, the first circuit includes the heater, and a midpoint of the first circuit is connected to one input portion of the operational amplifier, and the second circuit includes a D/A converter or a multiplexer, and an output portion of the D/A converter or the multiplexer is connected to the other input portion of the operational amplifier.

Advantageous Effect of Invention

According to the heater temperature control circuit of the present invention, the temperature accuracy of the heater can be more improved as compared with the conventional one. The present invention has an effect in which the setting temperature of the heater can be flexibly adjusted and changed, although the effect cannot be achieved by the conventional heater temperature control circuit.

DESCRIPTION OF EMBODIMENTS

Hereinafter, one embodiment of the present invention (hereinafter, abbreviated as "an embodiment") will be described in detail. Note that the present invention is not limited to the following embodiments, and various modifications may be possible without departing from the scope of the subject matter.

Figure 1:
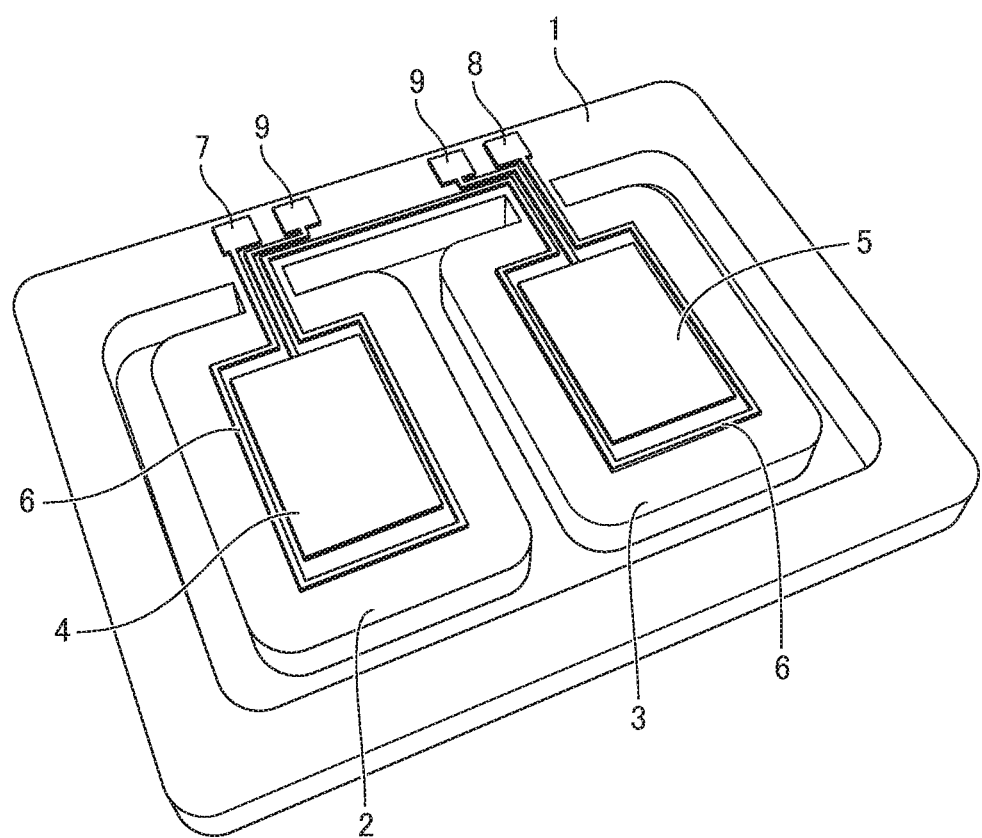
FIG. 1 is a perspective view illustrating an example of a sensor device of the present embodiment.

FIG. 1 is a perspective view illustrating an embodiment of a sensor device of the present embodiment. FIG. 1 illustrates an example of a contact combustion-type gas sensor, which is, for example, a hydrogen sensor capable of detecting a hydrogen concentration.

Reference numeral 1 illustrated in FIG. 1 denotes a quartz plate (quartz substrate) fabricated by cutting quartz crystals through etching or the like. Reference numeral 2 denotes a detecting quartz vibrator, and reference numeral 3 denotes a reference quartz vibrator.

As illustrated in FIG. 1, the detecting quartz vibrator 2 has a hydrogen reaction catalytic layer 4 on a quartz surface formed by cutting the quartz plate 1. The hydrogen reaction catalytic layer 4 is formed of, for example, a platinum film.

As illustrated in FIG. 1, the reference quartz vibrator 3 has a hydrogen non-reactive layer 5 on the quartz surface formed by cutting the quartz plate 1. The hydrogen non-reactive layer 5 is formed of, for example, a gold thin film.

Note that although not illustrated in the figure, the hydrogen reaction catalytic layer 4 and the hydrogen non-reactive layer 5 are formed on both sides of the quartz vibrators 2 and 3, respectively.

Incidentally, the platinum film serving as the hydrogen reaction catalytic layer 4 is required to be heated to a predetermined temperature or higher in order to exert a catalytic action. For this reason, as illustrated in FIG. 1, a linear heater 6 for heating is formed adjacent to the hydrogen reaction catalytic layer 4.

In addition, as illustrated in FIG. 1, the linear heater 6 for heating is also formed proximate to the hydrogen non-reactive layer 5.

In FIG. 1, the heater 6 is formed to surround the circumferences of the hydrogen reaction catalytic layer 4 and the hydrogen non-reactive layer 5, but this is just an example and does not limit the shape, arrangement and the like of the heater 6.

Note that it is preferable that the heater 6 for heating the hydrogen reaction catalytic layer 4 and the heater 6 for heating the hydrogen non-reactive layer 5 are made of, for example, the same material to have the same property. This is because a heat amount generated from the hydrogen reaction catalytic layer 4 is accurately detected by heating both of the hydrogen reaction catalytic layer 4 and the hydrogen non-reactive layer 5 under the same condition.

Terminals 9 illustrated in FIG. 1 are connected to an oscillation circuit (not illustrated) such as a Colpitts oscillator to measure a resonant frequency of the detecting quartz vibrator 2. In addition, the oscillation circuit is connected to a frequency measurement device (not illustrated).

An operational principle of the hydrogen sensor illustrated in FIG. 1 will be described. Firstly, electric power is supplied to the terminals 7 and 8 of the heater 6 to heat the heater 6. At this time, the heater 6 is controlled to have a predetermined temperature. The temperature control is performed by the heater temperature control circuit (described later). By virtue of this electric power supply, the detecting quartz vibrator 2 and the reference quartz vibrator 3 are preheated under the same condition. Here, the preheating refers to a process of increasing the temperature of the hydrogen reaction catalytic layer 4 such that the hydrogen reaction catalytic layer 4 can function as a catalyst.

In addition, the terminals 9 are each connected to the oscillation circuit. The quartz plates 2 and vibrate as thickness shear vibrators, and a frequency signal corresponding to the natural frequency is output from the oscillation circuit. The oscillation frequency of the oscillation circuit is measured by the frequency measurement device, and a resonant frequency of the detecting quartz vibrator 2 is measured.

Here, the resonant frequencies of the detecting quartz vibrator 2 and the reference quartz vibrator 3 are measured in a state in which the detecting quartz vibrator 2 and the reference quartz vibrator 3 have high temperatures through preheating.

In this state, when the air containing hydrogen flows, the hydrogen is oxidized by oxygen in the air by virtue of a catalytic action of the hydrogen reaction catalytic layer 4 of the hydrogen sensor. In response to this oxidation, the oxidation heat is generated, so that the temperature of the detecting quartz vibrator 2 increases to a preheating temperature or higher.

The reference quartz vibrator 3 includes the hydrogen non-reactive layer 5, so that hydrogen is not oxidized even when the air contains hydrogen. In addition, the temperature of the reference quartz vibrator 3 is maintained at the preheating temperature. That is, the detecting quartz vibrator 2 has a temperature equal to or higher than the preheating temperature by virtue of the oxidation heat of hydrogen, whereas the reference quartz vibrator 3 has a temperature maintained at the preheating temperature. Therefore, the detecting quartz vibrator 2 has a resonant frequency generated at a temperature that depends on the preheating temperature and the temperature increase caused by the oxidation heat of hydrogen. On the other hand, the reference quartz vibrator 3 has a resonant frequency generated at the preheating temperature.

Here, when the resonant frequency of the detecting quartz vibrator 2 and the resonant frequency of the reference quartz vibrator 3 are measured to take a difference therebetween, there is eliminated a factor corresponding to the temperature increase caused by the preheating. Accordingly, it is possible to detect only a factor of the frequency change of the detecting quartz vibrator 2 purely influenced by the oxidation heat of hydrogen.

In this manner, a hydrogen concentration in the air can be measured by measuring a frequency change caused by the oxidation heat of hydrogen.

A contact combustion-type gas sensor such as the above-described hydrogen sensor is heated by the heater 6 to have a temperature of about 100° C. to 350° C. to thereby activate the catalyst, whereby the gas to be measured can be detected.

Since the sensor sensitivity changes depending on the catalyst temperature, to improve the detection accuracy of the gas concentration, it is necessary to provide a heater temperature control circuit which can maintain a heater temperature at a target temperature.

As a result of the present inventors' earnest study, there has been developed a heater temperature control circuit which can reduce an error with respect to a target temperature of a heater by reducing the number of resistors used in a bridge circuit and control a heat temperature with higher accuracy than the conventional one. Hereinafter, the heater temperature control circuit of the present embodiment will be described in detail.

Figure 2:
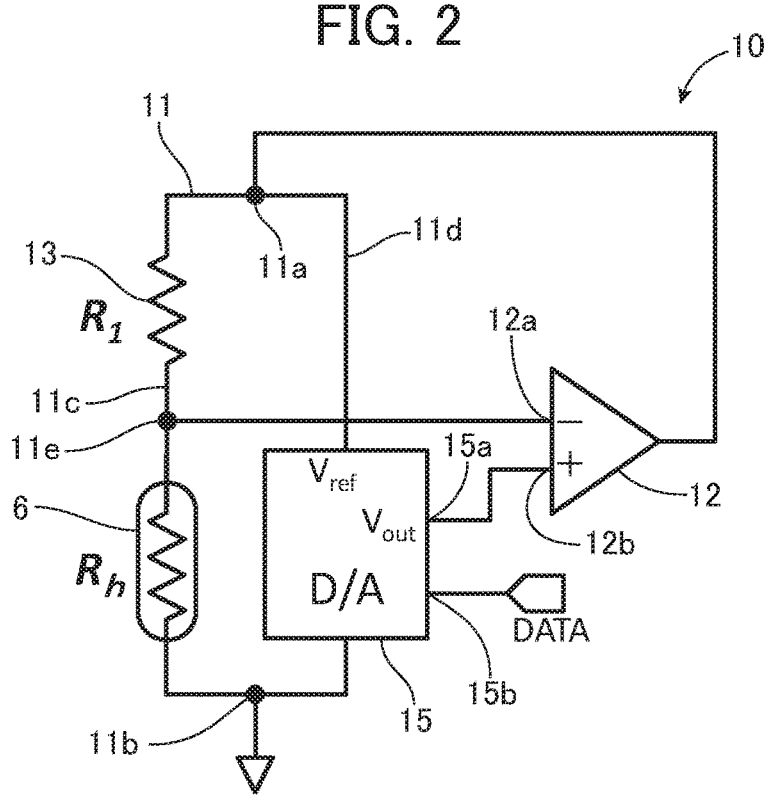
FIG. 2 is a circuit diagram illustrating a minimum unit of a heater temperature control circuit of the present embodiment.

FIG. 2 is a circuit diagram illustrating a minimum unit of the heater temperature control circuit of the present embodiment. As illustrated in FIG. 2, a heater temperature control circuit 10 of the present embodiment is configured to include a bridge circuit 11, and a driving operational amplifier 12 connected to the bridge circuit 11.

As illustrated in FIG. 2, in the bridge circuit 11, a first circuit 11c and a second circuit 11d are connected is parallel between an input portion 11a and a ground 11b.

As illustrated in FIG. 2, in the first circuit 11c, a resistor 13 and the heater 6 are connected in series. The resistor 13 is, for example, a fixed resistor. As illustrated in FIG. 1, a midpoint (output portion) 11e of the first circuit 11c is connected to an inverting input terminal ($V_{in}-$ terminal) 12a of the operational amplifier 12.

As illustrated in FIG. 2, a D/A converted (digital/analog converter) 15 is connected to the second circuit 11d. An output portion 15a of the D/A converter 15 is connected to a non-inverting input terminal ($V_{in}+$ terminal) 12b of the operational amplifier 12. Note that the D/A converter, as used herein, includes an external input terminal $V_{ref}$ of a reference voltage.

Figure 6:
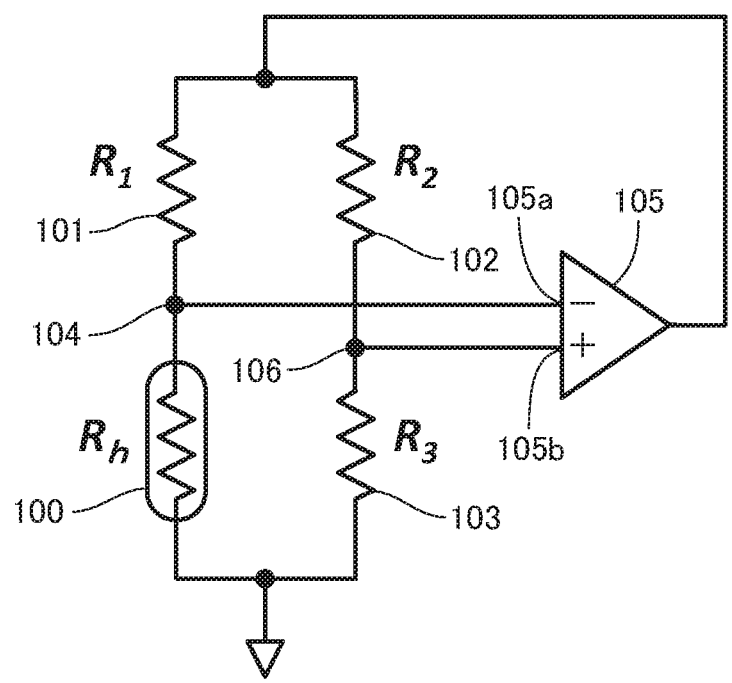
FIG. 6 is a circuit diagram illustrating a minimum unit of a conventional heater temperature control circuit.

As is apparent from the comparison with the conventional heater temperature control circuit (minimum unit) illustrated in FIG. 6, in the present embodiment, the resistors 102 and 103 (see FIG. 6) are eliminated from the bridge circuit 11, and instead the D/A converter 15 is connected to the second circuit 11d. In this way, in the present embodiment, the number of resistors used in the bridge circuit is only one, whereby the number of resistors can be minimized.

The equilibrium condition of the heater temperature control circuit of the present embodiment illustrated in FIG. 2 is expressed by the following expression (5).

$$\frac{V_{out}}{V_{ref}} = \frac{R_h}{R_1 + R_h} \qquad (5)$$

Here, $V_{out}$ out is an output value of the D/A converter 15. "$V_{ref}$" is a reference voltage to be applied to the input portion 11a. "$R_h$" is a target resistance value of the heater 6. "$R_1$" is a resistance value of the resistor 13.

An operational principle of the heater temperature control circuit 10 illustrated in FIG. 2 will be described. A voltage output (output value $V_{out}$) from the D/A converter 15 is input to the operational amplifier 12. On the other hand, the output from the midpoint 11e of the first circuit 11c is input to the operational amplifier 12 based on the division ratio of the resistance value $R_1$ and the resistance value of the heater 6. Accordingly, a differential output is obtained from the operational amplifier 12, and an amount of current flowing to the heater 6 varies depending on the differential output. Note that most of the current flows toward the first circuit 11c side. When the current flows in the heater 6, the heater temperature increases, and the resistance value of the heater 6 increases. When the heater 6 has reached the target temperature, the resistance value of the heater 6 becomes the target resistance value $R_h$, so that the output voltage of the operational amplifier 12 stops increasing. In the case where the temperature of the heater varies due to a change in external air temperature and the disturbance of wind or the like, the output voltage of the operational amplifier changes accordingly, thereby being stable at a voltage value balanced with the heat radiation from the heater.

When the above-described expression (5) is modified to obtain the expression for the target resistance value Rh of the heater 6, the following expression (6) is derived.

$$R_h = \frac{V_{out}}{V_{ref} - V_{out}} R_1 \quad (6)$$

Here, the above-described expression (6) can be modified as in the following expression (7) from the viewpoint of the resistance value tolerance and temperature coefficient of resistance (TCR) of the resistor 13 provided in the bridge circuit 11.

$$R_h = \frac{V_{out}}{V_{ref} - V_{out}} (1 + E_1 + E_{T1}) R_1 \quad (7)$$

$E_1$: Resistance value tolerance of resistor 13
$E_{T1}$: Error caused by temperature coefficient of resistance (TCR) of resistor 13
$E_T = TCR \times \Delta T_r$
$\Delta T_r$: External air temperature change By the way, in the present embodiment, the digital data (DATA) shown in the following expression (8) is input from a digital data input terminal 15b of the D/A converter 15.

$$DATA = \{R_h/(R_1 + R_h)\} \times (2^n - 1) \quad (8)$$

Where "n" is the number of bits of the D/A converter.

"$2^n - 1$" is shown in the above-described expression (8) is the full scale of the digital data. Accordingly, the full scale data can be converted to the digital data corresponding to the division ratio by multiplying the division ratio $\{R_h/(R_1 + R_h)\}$ with this full scale. Note that although the number of bits n is not limited, the D/A converter with 8 bits to 24 bits is available at an inexpensive price.

The digital data can be written from outside by using a general-purpose microcomputer or the like. Accordingly, the digital data can be arbitrarily set and changed. Examples of a communication scheme include, but are not particularly limited to, serial communication handling the serial data such as I²C and SPI and parallel communication handling the parallel data.

The target resistance value $R_h$ and the fixed resistance $R_1$ can be obtained from, for example, the catalog values of a manufacturer. These resistance values are set as appropriate and the digital data is written to the D/A converter 15. As illustrated in FIG. 2, the reference voltage tire $V_{ref}$ is input to the D/A converter 15. Accordingly, the output value $V_{out}$ can be obtained from the above-described expression (5), and is input to the operational amplifier 12.

Here, the target resistance value $R_h$ of the present embodiment is discussed. The target resistance value $R_h$ obtained from the equilibrium condition of the bridge circuit 11 is represented by the above-described expression (7). As apparent from the expression (7), in the present embodiment, the effect of the errors of the resistors 102 and 103 in the conventional circuit can be eliminated.

In addition, the accuracy of the D/A converter 15 can be considered using the number of bits and the specification value of the error. For example, the D/A converter 15 having an error of ± several LSE's at 16 bits can obtain the accuracy of several tens ppm ($10^{-5}$).

Therefore, as in the present embodiment, the error in the target resistance value $R_h$ obtained from the expression (7) can be reduced by using the D/A converter 15 instead of the resistors 102 and 103 (see FIG. 6).

Accordingly, in the present embodiment, the temperature accuracy of the heater 6 can be more improved as compared with the conventional one. Note that the calculation expression of the heater temperature is the same as the above-described expression (4), and the description thereof is omitted.

Next, the temperature error of the heater will be described with reference to, as a specific example, a platinum heater. Firstly, the temperature error was obtained in the conventional heater temperature control circuit illustrated in FIG. 6. While the target resistance value $R_h$ of the heater is 50Ω and TCR is +3900 ppm/° C. (pure platinum), the error was calculated using the tolerance ±5% and TCR=±100 ppm/° C. when the general-purpose resistors were used for the resistors 101, 102, and 103. As a result, the resistance deviation of the heater due to the tolerance was 8Ω at maximum, and was 41° C. in terms of temperature. That is, the conventional heater temperature control circuit resulted in the temperature error of 41° C. at maximum. Note that the following table 1 shows physical properties of the resistors used for the calculation.

TABLE 1

| Name | $R_1$ | $R_2$ | $R_3$ | $R_h$ |
|---|---|---|---|---|
| Type | | General-purpose resistor | | Platinum heater |
| Resistance value [Ω] | 10 | 10 k | 50 k | 50 |
| Tolerance [%] | ±5 | ±5 | ±5 | — |
| TCR [ppm/° C.] | ±100 | ±100 | ±100 | +3900 |

Note that the physical property values of the resistors shown in Table 1 are catalog values of the general-purpose products which are generally commercially available.

When being calculated by adding the temperature change of 20° C.±60° C., the resistance deviation of the heater due to two errors of the tolerance and the temperature coefficient of resistance TCR was 9Ω at maximum, resulting in the error of 47° C. in terms of temperature. Note that as is apparent from the calculation results, the resistance value tolerance has a dominant effect on the temperature error.

As another example, when a high accuracy resistor (tolerance: ±0.1%, TCR=±25 ppm/° C.) was used, the resistance deviation of the heater due to the tolerance was 0.4Ω at maximum, resulting in the error of 1.9° C. in terms of temperature. By using the high accuracy resistor, the temperature accuracy of the heater can be somewhat improved, but is still insufficient. Note that the following table 2 shows physical properties of the high accuracy resistors used for the calculation.

TABLE 2

| Name | $R_1$ | $R_2$ | $R_3$ | $R_h$ |
|---|---|---|---|---|
| Type | | High accuracy resistor | | Platinum heater |

TABLE 2-continued

| Name | $R_1$ | $R_2$ | $R_3$ | $R_h$ |
|---|---|---|---|---|
| Resistance value [Ω] | 10 | 10 k | 50 k | 50 |
| Tolerance [%] | ±0.1 | ±0.1 | ±0.1 | — |
| TCR [ppm/° C.] | ±25 | ±25 | ±25 | +3900 |

Note that the physical property values of the resistors shown in Table 2 are catalog values of the high accuracy products which are generally commercially available.

It has been found that when a variable resistor (volume) for temperature adjustment is used for the resistor (one or more of resistors $R_1$, $R_2$ and $R_3$), the resistance value accuracy is conversely deteriorated and the temperature error is increased. Furthermore, it has been found that when a heater with a temperature coefficient of resistance TCR smaller than a platinum bulk value is used, such as a thin film metallic heater or the like which is often used as a material of the microheater, the temperature deviation is doubly increased in proportion to the ratio of the temperature coefficient of resistance to the platinum bulk value.

In contrast, in the present embodiment, an element of the D/A converter 15 with differential nonlinearity of ±1 LSB at 16 bits is built in the circuit, for example. Consequently, only about 30 ppm (0.03%) of error occurs as the accuracy. Thus, it has been found that the accuracy can be improved by one digit or more than that in the case where the resistors 102 and 103 (see FIG. 6) are used as in the conventional heater temperature control circuit. As described above, is the present embodiment, the resistance deviation of the heater due to the tolerance is 0.16Ω at maximum, resulting in the error of 0.8° C. in terms of temperature. Thus, it has been found that the temperature error can be reduced to ±1° C. or lower.

Figure 3:
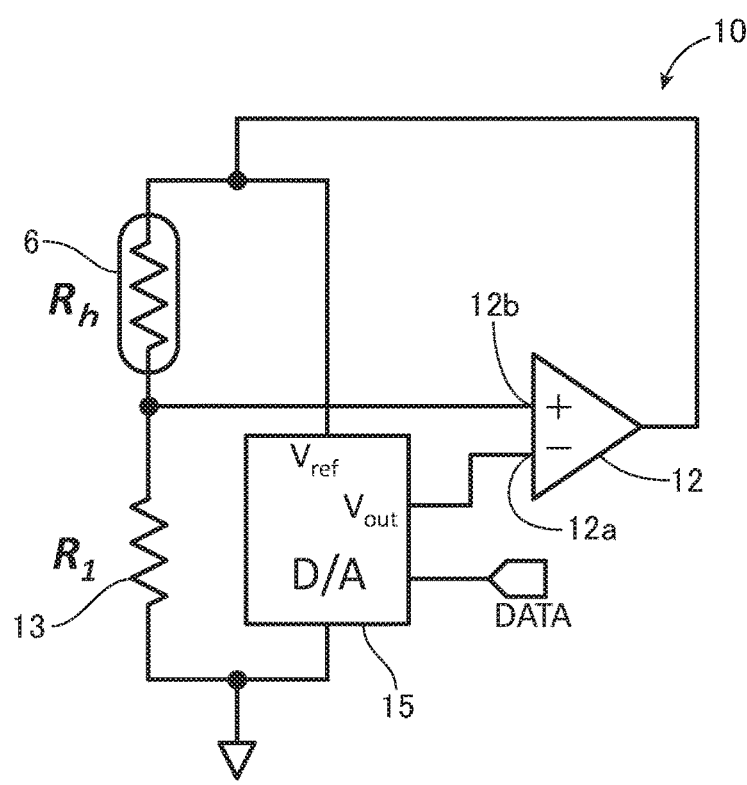
FIG. 3 is a circuit diagram illustrating a minimum unit of a heater temperature control circuit of the present embodiment which is partially different from that in FIG. 2.

In an embodiment in FIG. 3, the positions of the heater 6 and the resistor 13 are switched with respect to FIG. 2. Note that as illustrated in FIG. 3, the inverting input terminal 12a and non-inverting input terminal 12b of the operational amplifier 12 are reversed from FIG. 2. In addition, the equilibrium condition in the heater temperature control circuit in FIG. 3 can be obtained from the following expression (9).

$$\frac{V_{out}}{V_{ref}} = \frac{R_1}{R_1 + R_h} \quad (9)$$

Even when the positions of the heater 6 and the resistor 13 are switched as illustrated in FIG. 3, the heater temperature control circuit is operable in the same manner as that in FIG. 2, and the heater temperature can be maintained with high accuracy.

Incidentally, in the heater temperature control circuit using the D/A converter, a problem due to a positive feedback may occur depending on the initial state of the output from the D/A converter 15. That is, when an initial value of the output from the D/A converter 15 is 0 V, the heater temperature control circuit operates so that the output of the operational amplifier 12 is reduced until the digital data (DATA) is written. Then, when the output from the operational amplifier 12 becomes 0 V, a problem that the entire circuit is locked occurs.

Therefore, for example, it is necessary to devise the input stage of the operational amplifier 12, so that the output of the operational amplifier 12 does not become 0 V. Specifically, the positive voltage is applied temporarily to the non-inverting input terminal ($V_{in}$+ terminal) of the operational amplifier 12. Alternatively, the negative voltage is applied temporarily to the inverting input terminal ($V_{in}$− terminal) of the operational amplifier 12. Or, the positive voltage is applied temporarily to the $V_{ref}$ terminal of the D/A converter 15 and is adjusted so that the output of the operational amplifier 12 does not become 0 V. Note that each of the above-described configurations is merely an example and is not limited thereto.

In each of the heater temperature control circuits 10 illustrated in FIG. 2 and FIG. 3 as the minimum configuration, a delay element of a time constant of the heater 6 is included in the control system. Therefore, when the phase of the output signal is turned by 180°, the operational amplifier 12 causes an abnormal oscillation problem. For example, when the loop gain is larger than 1 at a frequency at which the phase is turned by 180° in the negative feedback control system, the oscillation condition at the frequency corresponding to the time constant of the feedback control system heater is established, resulting that the abnormal oscillation occurs.

Figure 4:
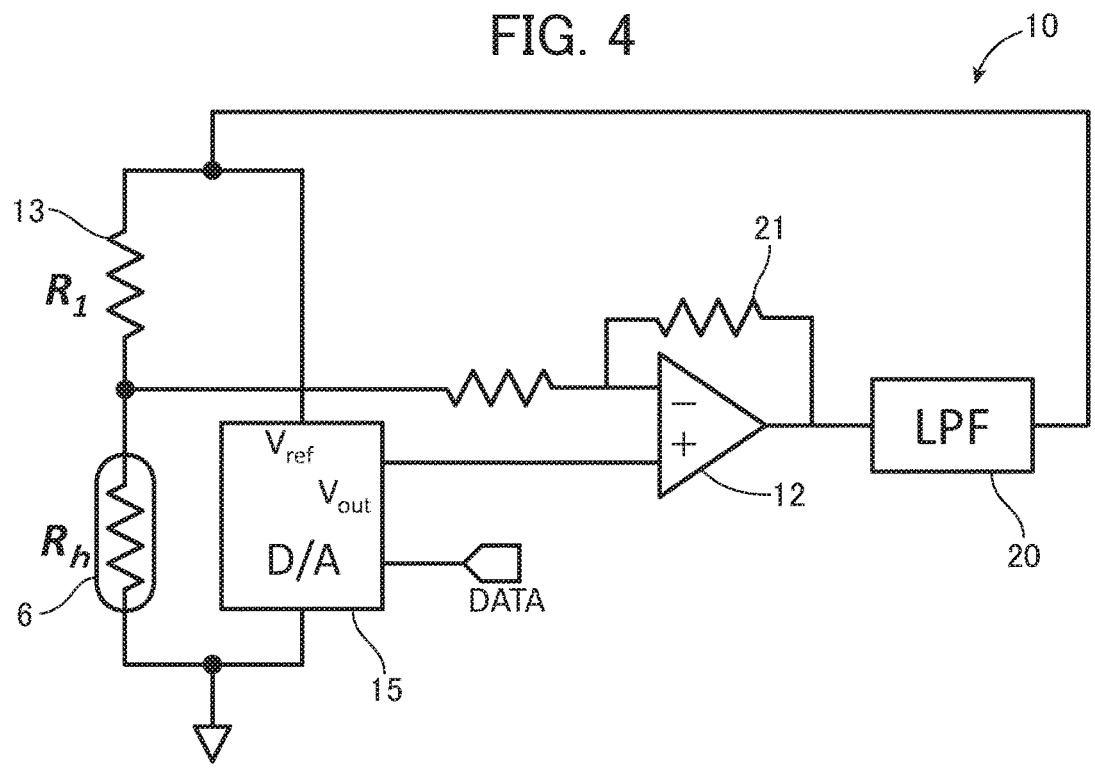
FIG. 4 is a circuit diagram illustrating an application example of the heater temperature control circuit illustrated in FIG. 2.

In the present embodiment, as in the application example illustrated in FIG. 4, a low-pass filter (LPF) 20 for preventing an abnormal oscillation is connected to the output stage of the operational amplifier 12. In FIG. 4, a feedback resistor 21 is added to the operational amplifier 12. Thus, by making a response frequency of the heater temperature control circuit 10 lower than the time constant of the heater 6, the loop gain can be reduced to 1 or less. In this way, the abnormal oscillation can be suppressed.

Note that when a response speed of the heater temperature control circuit 10 decreases, the heating time period required for the heater 6 to reach the target temperature becomes longer and the followability to the change in external air temperature is likely to be degraded. The range satisfying the condition that the loop gain is 1 or less can be widened by using the low-pass filter (LPF) 20 such as a high order filter and an active filter with a large damping factor. In this way, the response speed of the heater temperature control circuit 10 can be maximized.

Figure 5:
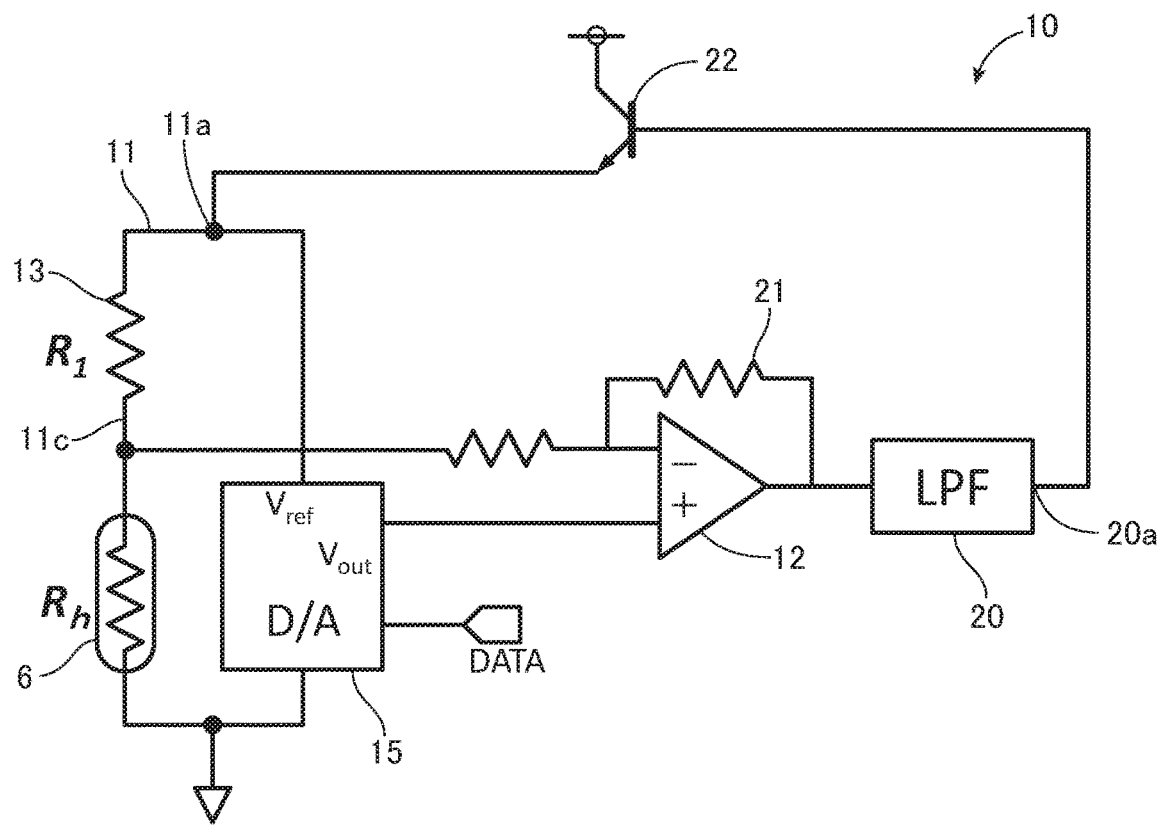
FIG. 5 is a circuit diagram illustrating an application example of the heater temperature control circuit illustrated in FIG. 2.

However, when the response is not emphasized, the circuit can be achieved with the minimum number of elements by using a first-order filter for the low-pass filter 20. FIG. 5 illustrates an application example in which a transistor for amplifying the current is added to the circuit configuration of FIG. 4. As illustrated in FIG. 5, transistor 22 for amplifying the current is connected between the input portion 11a of the bridge circuit and an output portion 20a of the low-pass filter 20. This makes it possible to amplify the current to the first circuit 11c of the bridge circuit 11. That is, an amount of current flowing in the heater 6 can be increased and the heater temperature control circuit 10 can drive even a heater with a large power consumption.

In the heater temperature control circuit 10 of the present embodiment, the output value $V_{out}$ to the operational amplifier 12 from the second circuit 11d of the bridge circuit 11 is controlled as a value obtained by multiplying the division ratio of the target resistance value $R_h$ of the heater and the resistance value $R_1$ with the reference voltage $V_{ref}$ of the bridge circuit 11, i.e., $V_{ref} \times \{R_h/(R_h+R_1)\}$ or $V_{ref} \times \{R_1/(R_h+R_1)\}$.

The above-described output value $V_{out}$ may be processed in an analog manner using a multiplexer in addition to the D/A converter 15.

The characteristic configuration of the present embodiment is collectively described below.

The present embodiment provides the heater temperature control circuit 10 that controls the temperature of the heater 6, the heater temperature control circuit including the bridge circuit 11 in which the first circuit 11c and the second circuit 11d are connected in parallel, and the operational amplifier 12 connected to the bridge circuit. In the first circuit 11c, the heater 6 and the resistor 13 are connected in series, and the midpoint 11e of the first circuit 11c is connected to one input portion (the inverting input terminal 12a or the non-inverting input terminal 12b) of the operational amplifier 12. The output value $V_{out}$ from the second circuit 11d is input to the other input portion (the non-inverting input terminal 12b or the inverting input terminal 12a) of the operational amplifier 12, the output value $V_{out}$ being obtained by multiplying the division ratio of the target resistance value $R_h$ of the heater 6 and the resistance value $R_1$ of the resistor 13 with the reference voltage of the bridge circuit 11.

In the present embodiment, the second circuit 11d includes the D/A converter 15 or the multiplexer, and it is preferable that the output portion of the D/A converter 15 or the multiplexer is connected to the other input portion of the operational amplifier 12.

In addition, in the present embodiment, the second circuit 11d includes the D/A converter 15, and it is preferable that the digital data obtained by multiplying "$2^n-1$" ("n" is the number of bits of the D/A converter) with the division ratio is input to the D/A converter 15.

The present embodiment provides the heater temperature control circuit 10 that controls the temperature of the heater 6, the heater temperature control circuit 10 including the bridge circuit 11 in which the first circuit 11c and the second circuit 11d are connected in parallel, and the operational amplifier 12 connected to the bridge circuit 11. The first circuit 11c includes the heater 6, and the midpoint 11e of the first circuit 11c is connected to one input portion (the inverting input terminal 12a or the non-inverting input terminal 12b) of the operational amplifier 12. The second circuit 11d includes the D/A converter 15 or the multiplexer, and the output portion of the D/A converter or the multiplexer is connected to the other input portion (the non-inverting input terminal 12b or the inverting input terminal 12a) of the operational amplifier 12.

In the present embodiment, it is preferable that the low-pass filter 20 is connected to the output portion side of the operational amplifier 12.

In the present embodiment, it is preferable that the transistor 22 for amplifying the current is connected between the input portion of the bridge circuit 11 and the output portion of the low-pass filter 20.

The sensor device (e.g., a hydrogen sensor) of the present embodiment includes sensor elements (e.g., the detecting quartz vibrator 2 and the reference quartz vibrator 3), the heater 6 that applies heat to the sensor elements, and the heater temperature control circuit 10 that controls the temperature of the heater 6. The heater temperature control circuit 10 includes the bridge circuit 11 in which the first circuit 11c and the second circuit 11d are connected in parallel, and the operational amplifier 12 connected to the bridge circuit 11. In the first circuit 11c, the heater 6 and the resistor 13 are connected in series, and the midpoint 11e of the first circuit 11c is connected to one input portion (the inverting input terminal 12a or the non-inverting input terminal 12b) of the operational amplifier 12. The output value $V_{out}$ from the second circuit 11d is input to the other input portion (the non-inverting input terminal 12b or the inverting input terminal 12a) of the operational amplifier 12, the output value $V_{out}$ being obtained by multiplying the division ratio of the target resistance value $R_h$ of the heater 6 and the resistance value $R_1$ the resistor with the reference voltage $V_{ref}$ of the bridge circuit 11.

The sensor device (e.g., a hydrogen sensor) of the present embodiment includes sensor elements (e.g., the detecting quartz vibrator 2 and the reference quartz vibrator 3), the heater 6 that applies heat to the sensor elements, and the heater temperature control circuit 10 that controls the temperature of the heater 6. The heater temperature control circuit 10 includes the bridge circuit 11 in which the first circuit 11c and the second circuit 11d are connected in parallel, and the operational amplifier 12 connected to the bridge circuit 11. The first circuit 11c includes the heater 6, and the midpoint 11e of the first circuit 11c is connected to one input portion (the inverting input terminal 12a or the non-inverting input terminal 12b) of the operational amplifier 12. The second circuit 11d includes the D/A converter 15 or the multiplexer, and the output portion of the D/A converter or the multiplexer is connected to the other input portion (the non-inverting input terminal 12b or the inverting input terminal 12a) of the operational amplifier 12.

In the present embodiment, it is preferable that the sensor element detects the gas concentration.

The effects of using the heater temperature control circuit 10 in the present embodiment will be described. Firstly, the temperature accuracy of the heater 6 can be more improved as compared with the conventional one. Secondly, the temperature setting of the heater 6 can be flexibly adjusted and changed. That is, in the heater temperature control circuit 10 using the D/A converter 15, the setting temperature can be freely changed during the heater heating operation, although it cannot be achieved in the bridge circuit including the fixed resistor or the semi-fixed resistor.

For example, the thermal stress to the sensor elements can be lessened by switching the temperature of the heater 6 to detect a plurality of gases during operation of the sensor device or gradually heating the heater 6 from the room temperature. In addition, the temperature of the heater is temporarily set to a temperature higher than the original setting temperature, and can be adjusted so that the heater temperature has high rising speed.

However, the voltage drop caused by the heater 6 and the resistor 13, i.e., the reference voltage is limited to a range not exceeding the maximum output voltage of the operational amplifier 12.

Note that even in the heater temperature control circuit including the conventional bridge circuit, the resistance value accuracy can be temporarily improved by coinciding the resistance value with the volume, but the drift of the resistance value due to vibration and backlash cannot be avoided. Furthermore, the temperature coefficient of resistance (TCR) is larger than that of the high accuracy resistor (see Table 2). Therefore, in the heater temperature control circuit 10 of the present embodiment, the temperature accuracy of the heater can be improved more effectively than the conventional one having the above-described configuration.

In the conventional art, a method of detecting the current flowing in the heater with a shunt resistor (resistor for current detection) and dynamically controlling the voltage to be applied is used, but the microheater of 1 W or less is greatly affected by an error caused by the resistance value of the shunt resistor. Accordingly, in the heater temperature control circuit of the present embodiment, the temperature accuracy of the heater can be improved more effectively than the conventional one having the above-described configuration.

A control microcomputer used for voltage control in the control circuit using the shunt resistor requires a process in real time such as PID control, and thus, the process occupies the CPU. In contrast, in the present embodiment, since the circuit control is independently performed by performing writing the digital data to the D/A converter 15 or controlling the division ratio to the multiplexer once at a time of starting of the heater temperature control circuit, the load applied to the microcomputer is extremely slight.

Note that the heater temperature control circuit of the present embodiment can be applied not only to the contact combustion-type gas sensor such as a hydrogen sensor illustrated in FIG. 1 but also for temperature control of various sensor devices on which an oxide semiconductor type gas sensor or a microheater such as a thermal sensor including a flow sensor is mounted.

INDUSTRIAL APPLICABILITY

According to the heater temperature control circuit of the present invention, the heater temperature accuracy can be improved, and therefore the heater temperature control circuit can be applied not only to a contact combustion-type gas sensor, an oxide semiconductor type gas sensor, or a gas sensor, but also to various devices for which the sensor accuracy is required, such as an MEMS sensor having a heater.

This application claims the benefit of Japanese Application No. 2017-230501, filed Nov. 30, 2017, which is hereby incorporated by reference herein in its entirety.

The invention claimed is:

1. A heater temperature control circuit that controls a temperature of a heater, the heater temperature control circuit comprising:
a bridge circuit provided with
an input portion,
a ground, and
a first circuit and a second circuit that are each connected in parallel between the input portion and the ground; and
an operational amplifier connected to the bridge circuit,
wherein the first circuit includes the heater connected in series with a resistor, and a midpoint of the first circuit is connected to one input portion of the operational amplifier,
wherein the second circuit includes a D/A converter or a multiplexer, and an output portion of the D/A converter or the multiplexer is connected to the other input portion of the operational amplifier,
wherein an equilibrium condition of the heater temperature control circuit is expressed by the following equation (5):

$$\frac{V_{out}}{V_{ref}} = \frac{R_h}{R_1 + R_h}, \tag{5}$$

wherein $V_{out}$ denotes an output value of the D/A converter or the multiplexer, wherein $V_{ref}$ denotes a voltage applied to the input portion of the bridge circuit,
wherein $R_h$ denotes a resistance value when the heater reaches a target temperature, and
wherein $R_1$ denotes a resistance value of the resister that is connected to the first circuit.

2. The heater temperature control circuit according to claim 1,
wherein digital data obtained by multiplying "$2^n-1$" ("n" is the number of bits of the D/A converter) with $\{R_h/(R_1+R_h)\}$ is input to the D/A converter.

3. The heater temperature control circuit according to claim 1,
wherein a low-pass filter is connected to an output portion side of the operational amplifier.

4. The heater temperature control circuit according to claim 3,
wherein a transistor for amplifying a current is connected between the input portion of the bridge circuit and an output portion of the low-pass filter.

5. A sensor device, comprising:
a sensor element;
a heater that applies heat to the sensor element; and
a heater temperature control circuit that controls a temperature of the heater,
wherein the heater temperature control circuit includes:
a bridge circuit provided with
an input portion,
a ground, and
a first circuit and a second circuit that are each connected in parallel
between the input portion and the ground; and
an operational amplifier connected to the bridge circuit,
wherein the first circuit includes the heater connected in series with a resistor, and a midpoint of the first circuit is connected to one input portion of the operational amplifier,
wherein the second circuit includes a D/A converter or a multiplexer, and an output portion of the D/A converter or the multiplexer is connected to the other input portion of the operational amplifier,
wherein an equilibrium condition of the heater temperature control circuit is expressed by the following equation (5):

$$\frac{V_{out}}{V_{ref}} = \frac{R_h}{R_1 + R_h}, \tag{5}$$

wherein $V_{out}$ denotes an output value of the D/A converter or the multiplexer,
wherein $V_{ref}$ denotes a voltage applied to the input portion of the bridge circuit,
wherein $R_h$ denotes a resistance value when the heater reaches a target temperature, and
wherein $R_1$ denotes a resistance value of the resister that is connected to the first circuit.

6. The sensor device according to claim 5,
wherein the sensor element detects a gas concentration.

* * * * *